United States Patent
Durkin et al.

(10) Patent No.: US 10,278,751 B2
(45) Date of Patent: May 7, 2019

(54) METHOD OF PROVIDING INTERCONNECTED PORES WITH A GROWTH-PROMOTING MEDIUM FOR CONTROLLED TISSUE INTEGRATION

(71) Applicant: Proxy Biomedical Limited, Galway (IE)

(72) Inventors: Tony Durkin, Galway (IE); Cormac Breathnach, Galway (IE); Niall Rooney, Galway (IE); Peter Gingras, Shaker Heights, OH (US)

(73) Assignee: PROXY BIOMEDICAL LIMITED, Galway (IE)

(*) Notice: Subject to any disclaimer, the term of this patent is extended or adjusted under 35 U.S.C. 154(b) by 485 days.

(21) Appl. No.: 15/027,779

(22) PCT Filed: Oct. 13, 2014

(86) PCT No.: PCT/EP2014/071901
§ 371 (c)(1),
(2) Date: Apr. 7, 2016

(87) PCT Pub. No.: WO2015/052346
PCT Pub. Date: Apr. 16, 2015

(65) Prior Publication Data
US 2016/0242831 A1 Aug. 25, 2016

(30) Foreign Application Priority Data
Oct. 11, 2013 (IE) .................................. S2013/0313

(51) Int. Cl.
*A61B 17/04* (2006.01)
*A61B 17/84* (2006.01)
(Continued)

(52) U.S. Cl.
CPC ............ *A61B 17/84* (2013.01); *A61B 17/866* (2013.01); *A61F 2/28* (2013.01); *A61F 2/2846* (2013.01);
(Continued)

(58) Field of Classification Search
None
See application file for complete search history.

(56) References Cited

U.S. PATENT DOCUMENTS

| 5,348,788 A | 9/1994 | White | |
| 2005/0112397 A1* | 5/2005 | Rolfe | A61B 17/8605 |
| | | | 428/593 |

(Continued)

FOREIGN PATENT DOCUMENTS

WO 2006053291 A2 5/2006

OTHER PUBLICATIONS

PCT International Search Report and Written Opinion for PCT/EP2014/071901, dated Dec. 5, 2014, pp. 1-10.

*Primary Examiner* — Sameh Boles
(74) *Attorney, Agent, or Firm* — Tarolli, Sundheim, Covell & Tummino LLP

(57) ABSTRACT

The present invention is concerned with a method of manufacturing a tissue-integration device, and a tissue-integration device so produced, the method comprising the steps of wrapping a porous sheet of material around a mandrel in order to create overlapping layers of the porous sheet material, the wrapped mandrel then being placed in a mould in order to apply pressure and heat to the overlapping layers in order to effect the lamination thereof such as to form a device having spaces defined by overlapping pores of the adjacent layers.

9 Claims, 12 Drawing Sheets

(51) Int. Cl.
    *A61F 2/08*         (2006.01)
    *A61B 17/86*      (2006.01)
    *A61L 27/54*      (2006.01)
    *A61L 27/56*      (2006.01)
    *A61L 31/14*      (2006.01)
    *A61L 31/16*      (2006.01)
    *A61F 2/28*       (2006.01)
    *A61F 2/30*       (2006.01)

(52) U.S. Cl.
    CPC ............... *A61L 27/54* (2013.01); *A61L 27/56* (2013.01); *A61L 31/146* (2013.01); *A61L 31/16* (2013.01); *A61F 2002/2817* (2013.01); *A61F 2002/30224* (2013.01); *A61F 2002/30235* (2013.01); *A61F 2002/30772* (2013.01); *A61F 2002/30784* (2013.01); *A61F 2002/30971* (2013.01); *A61L 2430/02* (2013.01)

(56) References Cited

U.S. PATENT DOCUMENTS

| | | |
|---|---|---|
| 2005/0276791 A1 | 12/2005 | Hansford et al. |
| 2007/0116734 A1 | 5/2007 | Akash |
| 2010/0042215 A1 | 2/2010 | Stalcup et al. |

\* cited by examiner

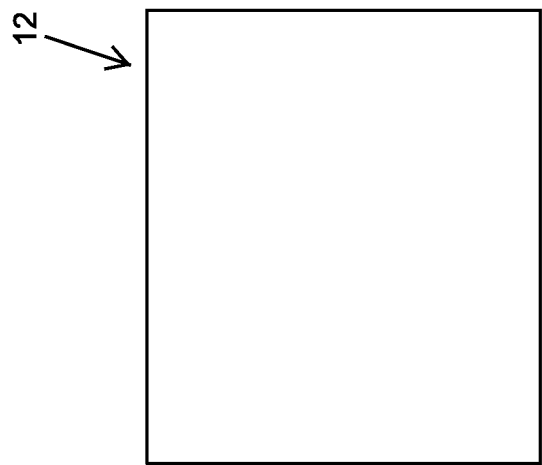
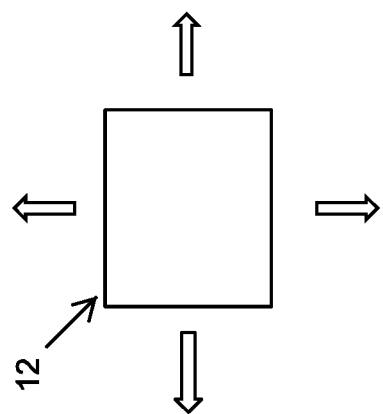
Fig. 1a

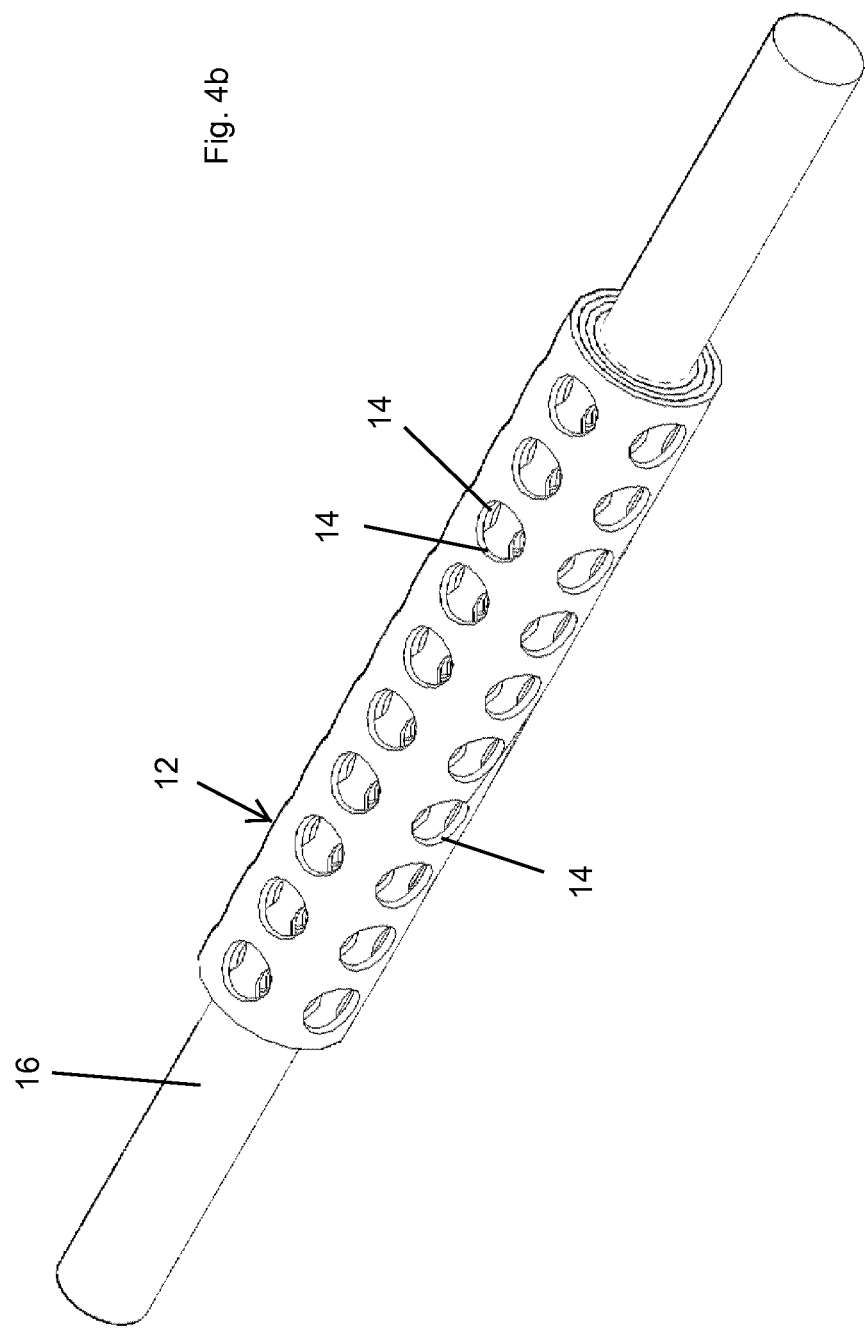

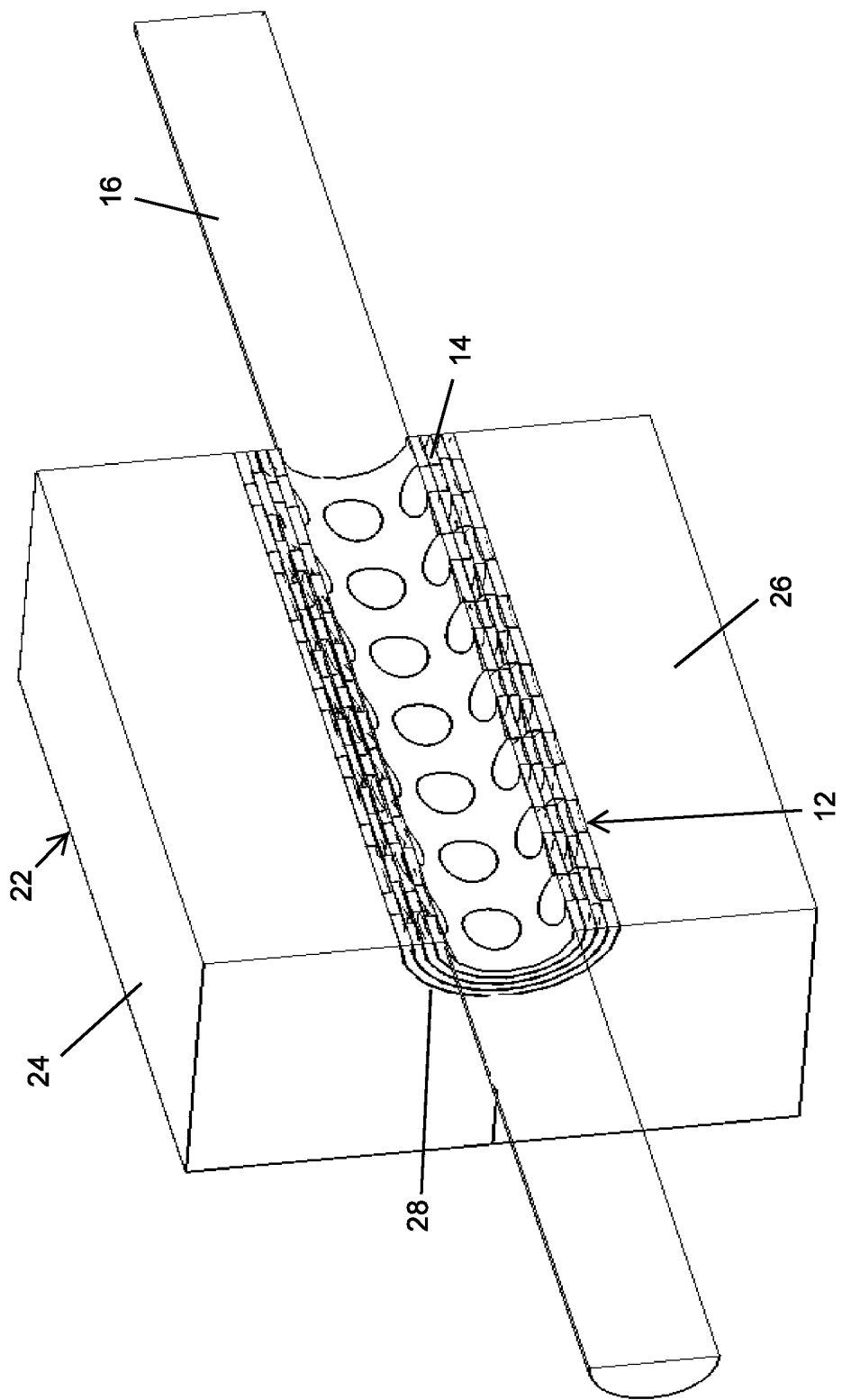

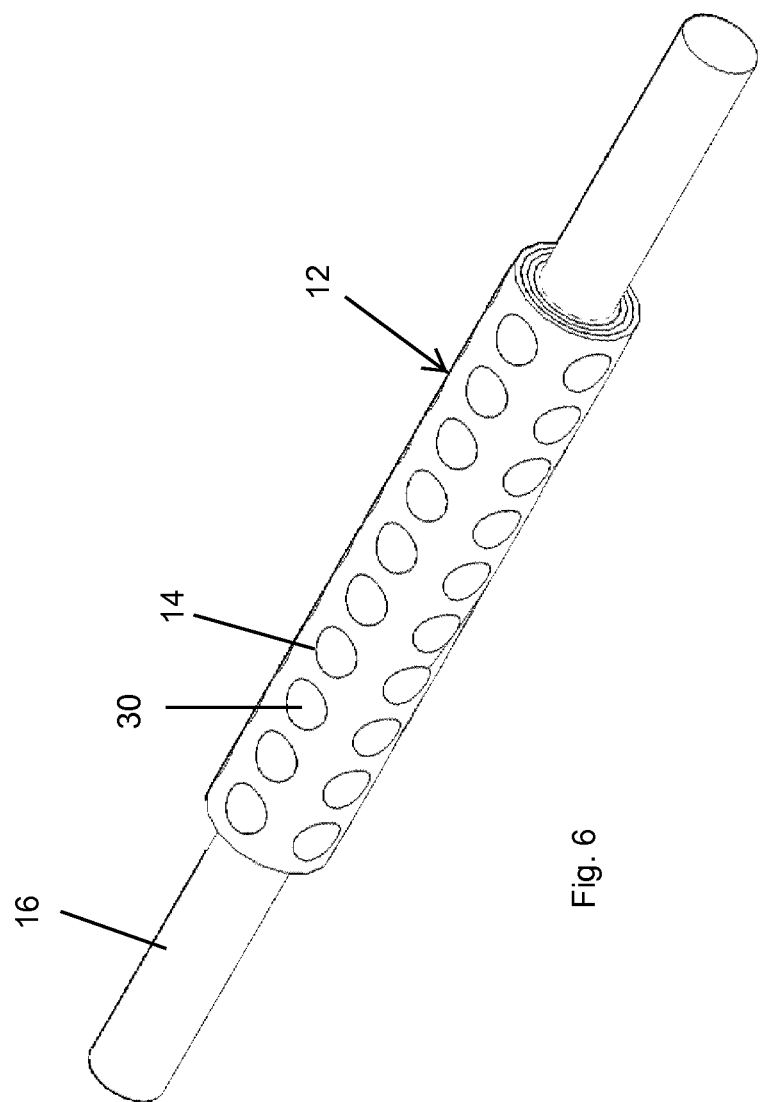

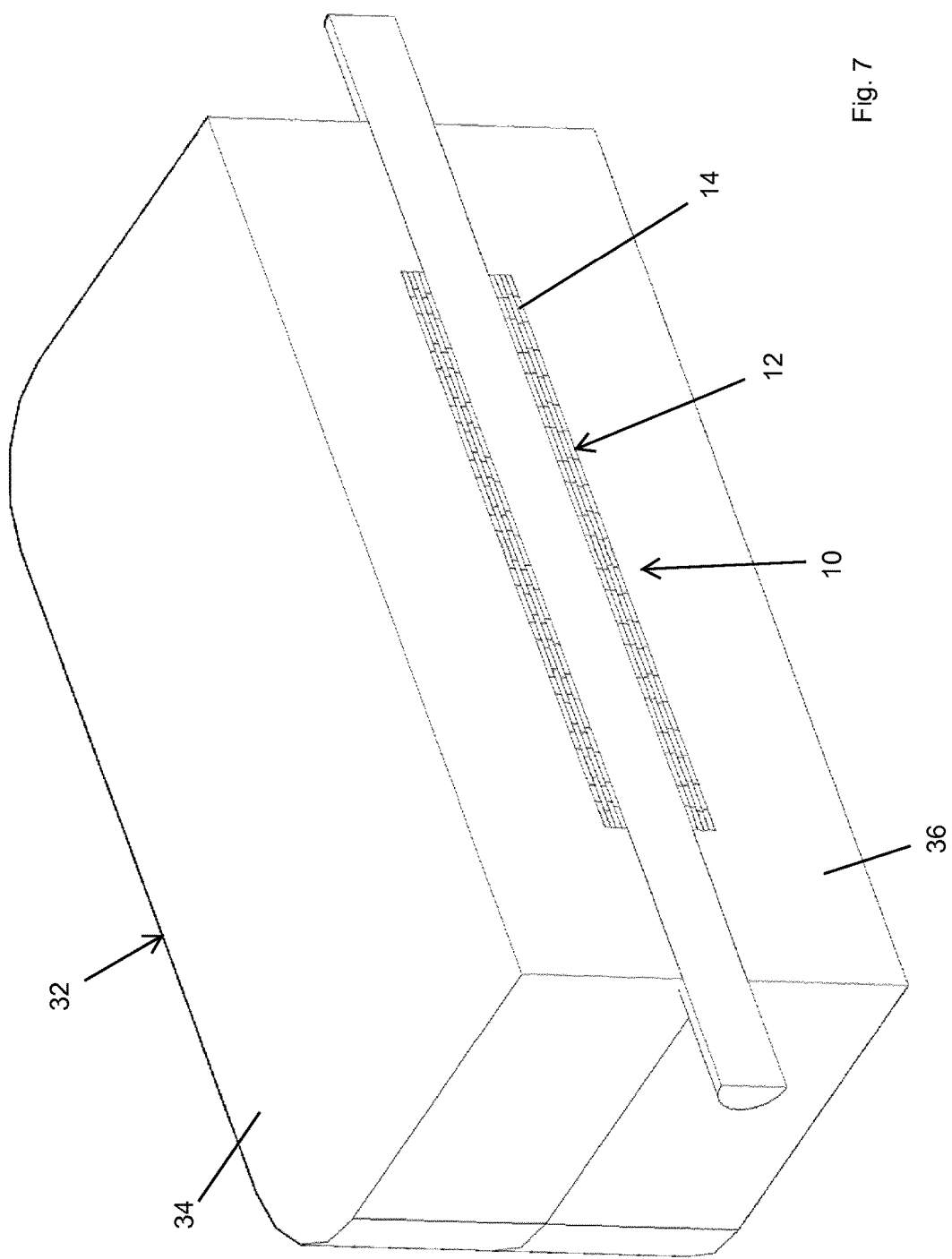

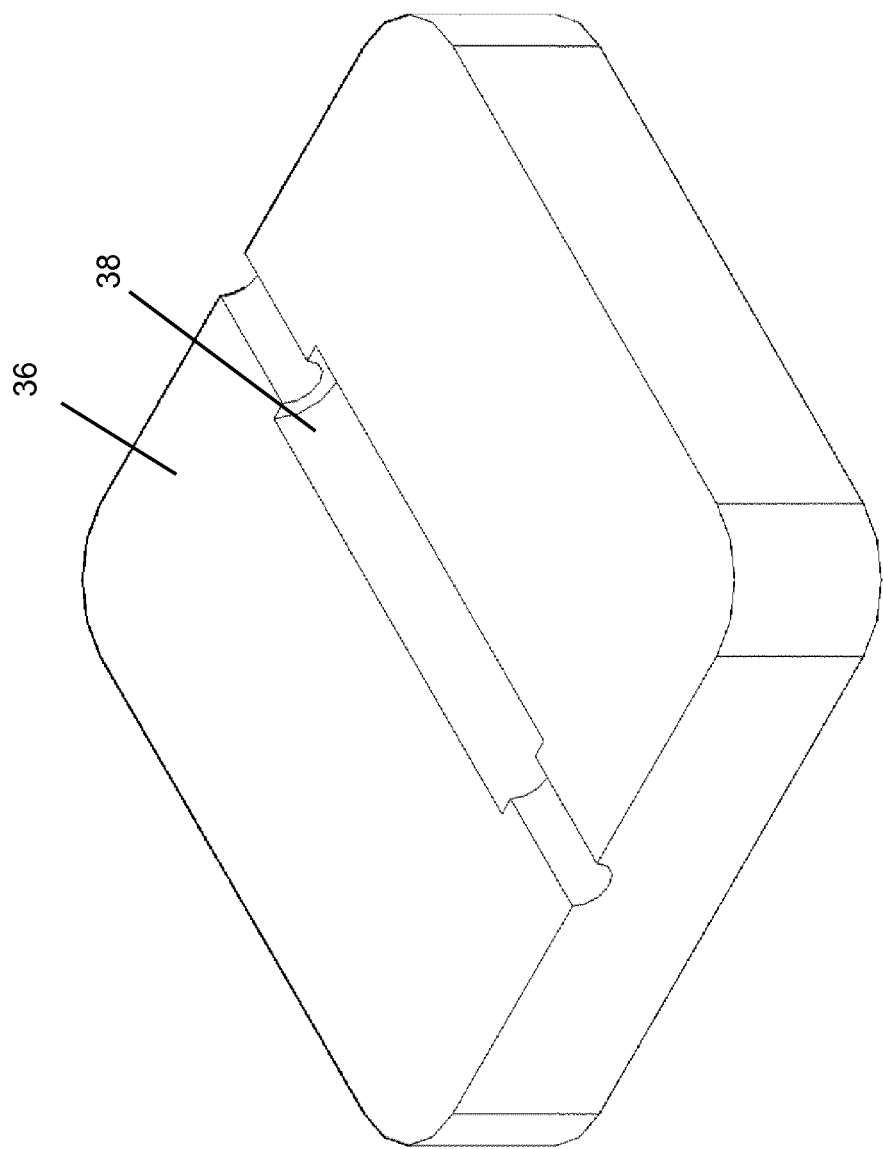

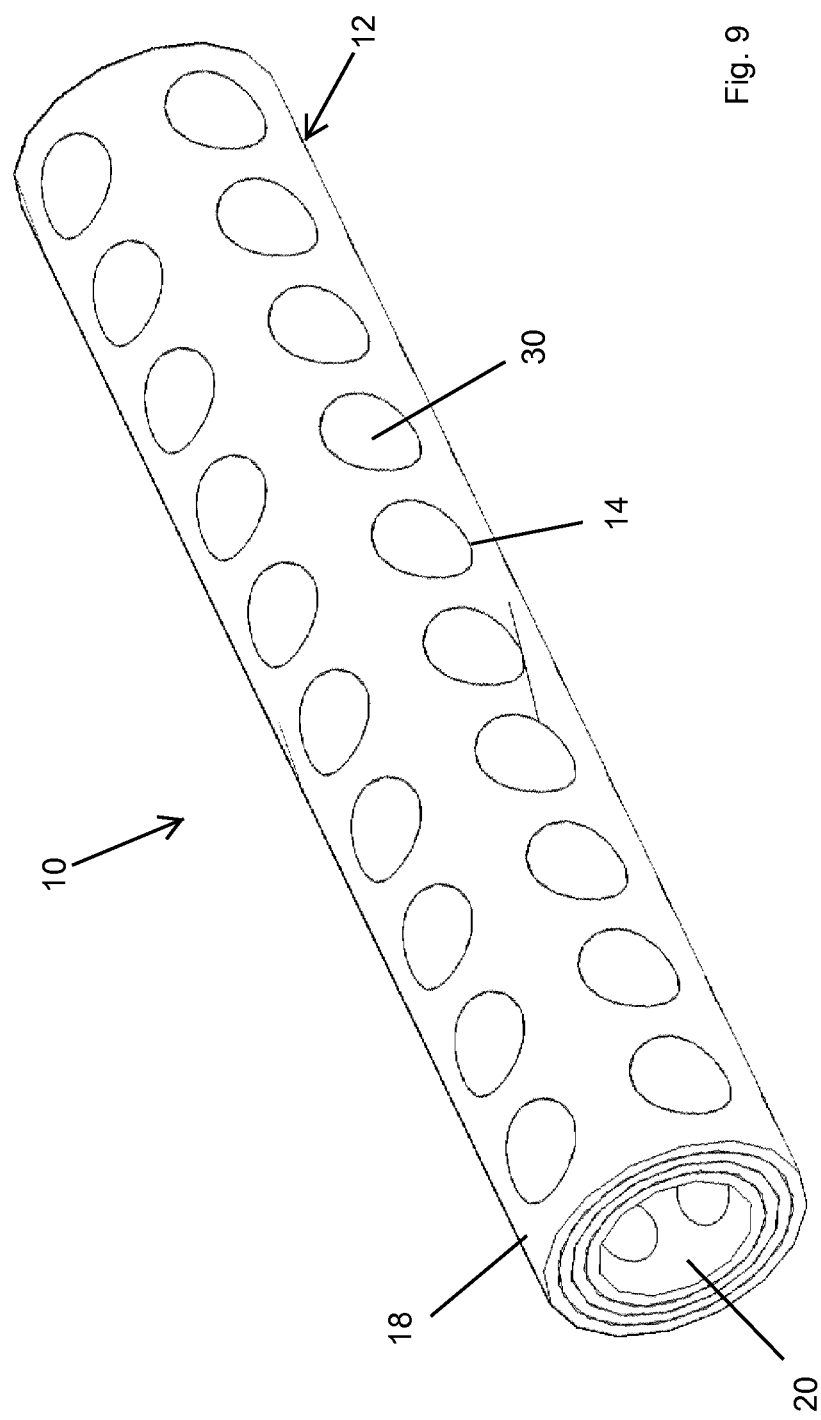

METHOD OF PROVIDING INTERCONNECTED PORES WITH A GROWTH-PROMOTING MEDIUM FOR CONTROLLED TISSUE INTEGRATION

RELATED APPLICATIONS

The present application is a U.S. National Stage under 35USC 371 patent application, claiming priority to Ser. No. PCT/EP2014/071901, filed on Oct. 13, 2014, which claims priority from S2013/0313, filed on Oct. 11, 2013, both of which are incorporated herein by reference.

FIELD OF THE INVENTION

The present invention relates to the provision of a defined or controlled tortuous path(s) of connected pores within a multi-layer structure and through which a relevant growth-promoting medium can be positioned with the purpose of facilitating controlled tissue integration via a tortuous path across the multi-layer structure. The invention further relates to a method of manufacturing such a structure, for example but in no way limited to, tissue-regeneration devices or the like.

BACKGROUND OF THE INVENTION

Many surgical procedures require or involve the use of internal tethering of damaged bone or other tissue in order to fix the bone or tissue in position in order to address a misalignment, instability, and/or to enable the healing process to progress, for example allowing bone or tendon regrowth at a damage area. In order to facilitate such tethering it is often necessary to employ some form of bone or tissue anchor or similar fixation device which serves as a fixed point to which a suture may be anchored, in order to allow a tendon or ligament to be suture and thus secured to the bone. Fixation devices may also be use to enable additional surgical apparatus to be secured as required.

Such fixation devices may take many forms, for example an externally threaded bone screw, pin, plate or other, which may be threaded into a suitable hole formed in a section of bone, and which will therefore, once located, secure a suture to the bone which may then be utilised to achieve fixation of tendons or ligaments to the respective bone, for example when performing a rotator cuff repair or the like.

Commercially produced surgical fixation tools such as screws, pins, anchors, etc. are typically injection moulded from a suitable material such as a polymer or the like. These injection moulded parts can be manufactured from a single resin or a polymer mix, which is typically in the form of resin combined with a growth promoting medium, for example tricalciumphosphate (TCP) or any other suitable alternative. These mixes may vary in composition, for example containing 80% polymer to 20% growth promoting medium. When a mix of polymer and growth promoting medium is injected into the tool cavity in order to mould the fixation tool it is virtually impossible to control the distribution of growth promoting medium and as a result it is randomly spread throughout the cavity. Growth promoting medium that resides sub-surface of the final moulded product is effectively locked in by the surrounding polymer resin and is not readily available to be decalcified in order to promote bone ingrowth and/or bone regrowth once the fixation tool has been implanted.

It is therefore an object of the present invention to provide a tissue-integration device and a method of manufacturing same, which addresses some of the above mentioned problems of the prior art.

SUMMARY OF THE INVENTION

According to a first aspect of the invention there is provided a method of manufacturing a tissue-integration device, the method comprising the step of: overlapping layers of a porous sheet material to form the device and such as to create spaces defined by overlapping pores of adjacent layers.

Preferably, the method comprises the step of at least partially filling at least some of the pores with a growth-promoting medium before or after the overlapping step.

Preferably, the method comprises the step of rolling the sheet material into a tube of concentric layers.

Preferably, the method comprises the step of wrapping the sheet material around a mandrel to establish the layers of the device.

Preferably, the method comprises the step of compressing the layers together to at least partially laminate the layers of the device.

Preferably, the method comprises the step of forming an outer profile on the device during the compression step.

Preferably, the compression step is undertaken in two stages.

Preferably, the first stage in the compression step comprises applying pressure to the layers before the addition of the growth-promoting medium to at least partially laminate the layers.

Preferably, the second stage in the compression step comprises applying pressure to the partially laminated layers following the addition of the growth-promoting medium.

Preferably, the method comprises the step of forming an outer profile on the device during the second stage of the compression step.

Preferably, the method comprises overlapping the pores of adjacent layers such as to create at least one pathway between an outer and an inner surface of the device.

Preferably, the method comprises the step of applying heat to the sheet material during the compression step.

Preferably, the method comprises the step of orienting at least one of the layers of sheet material prior to overlapping.

Preferably, multiple layers of sheet material are oriented prior to overlapping and the orientation is varied between overlapping layers.

According to a second aspect of the present invention there is provided a tissue-integration device comprising a plurality of layers of a porous sheet material arranged such that at least some of the pores of adjacent layers at least partially overlap.

Preferably, the device comprises a growth-promoting medium at least partially filling at least some of the pores.

Preferably, the layers are at least partially laminated.

Preferably, the device comprises an outer profile having surface formations.

Preferably, the device comprises a tube of concentric layers.

Preferably, the device comprises an outer surface and an inner surface, and at least one pathway between the outer and inner surfaces defined by the overlapping pores.

Preferably, the device comprises a means of securing a tether.

Preferably, at least one of the layers is oriented prior to layering.

Preferably, multiple layers of the sheet material are oriented prior to layer and in which the orientation is varied between overlapping layers.

Preferably, the device comprises a tissue fixation device.

Preferably, the device comprises a tissue scaffold.

As used herein, the terms "tissue" and "tissue-integration device" are intended to mean, respectively, tissue such as bone, cartilage or muscle, and a device for integration and therefore fixation onto and/or into such tissue, for example in the form of an anchor, surgical screw, pin, rod, plate or the like, in addition to bone or tissue scaffold.

BRIEF DESCRIPTION OF THE DRAWINGS

The present invention will now be described with reference to the accompanying drawings, in which:

FIG. 1a illustrates a schematic representation of the process of stretching a cast resin blank into a sheet of material having a larger surface area but reduced thickness;

FIG. 4b illustrates a perspective view of the sheet material fully wound onto a mandrel;

FIG. 5 illustrates a sectioned view of the sheet wound mandrel mounted in a compression tool;

FIG. 6 illustrates the partially laminated layers on the mandrel, a growth-promoting medium having been applied to the layers;

FIG. 7 illustrates a sectioned view of the laminated sheet wound mandrel contained within a further compression tool;

FIG. 8 illustrates a perspective view of a lower half of the compression tool of FIG. 7;

FIG. 9 illustrates a perspective view of the final formed device; and

DETAILED DESCRIPTION OF THE DRAWINGS

Referring now to FIGS. 1 to 9 of the accompanying drawings there is illustrated an exemplary embodiment of a tissue-integration device according to the present invention, generally indicated as 10, for use in surgical procedures, in particular securing or anchoring tissue, bone or the like, as well as securing additional surgical apparatus to bone, cartilage or other suitable tissue, while promoting tissue in-growth to the device 10. The device 10 is shown in final form in FIG. 9, and in FIGS. 1-8 as a partially formed product being progressed through the sequential stages in the method of manufacturing the device 10 according to the invention.

Figure 1B:
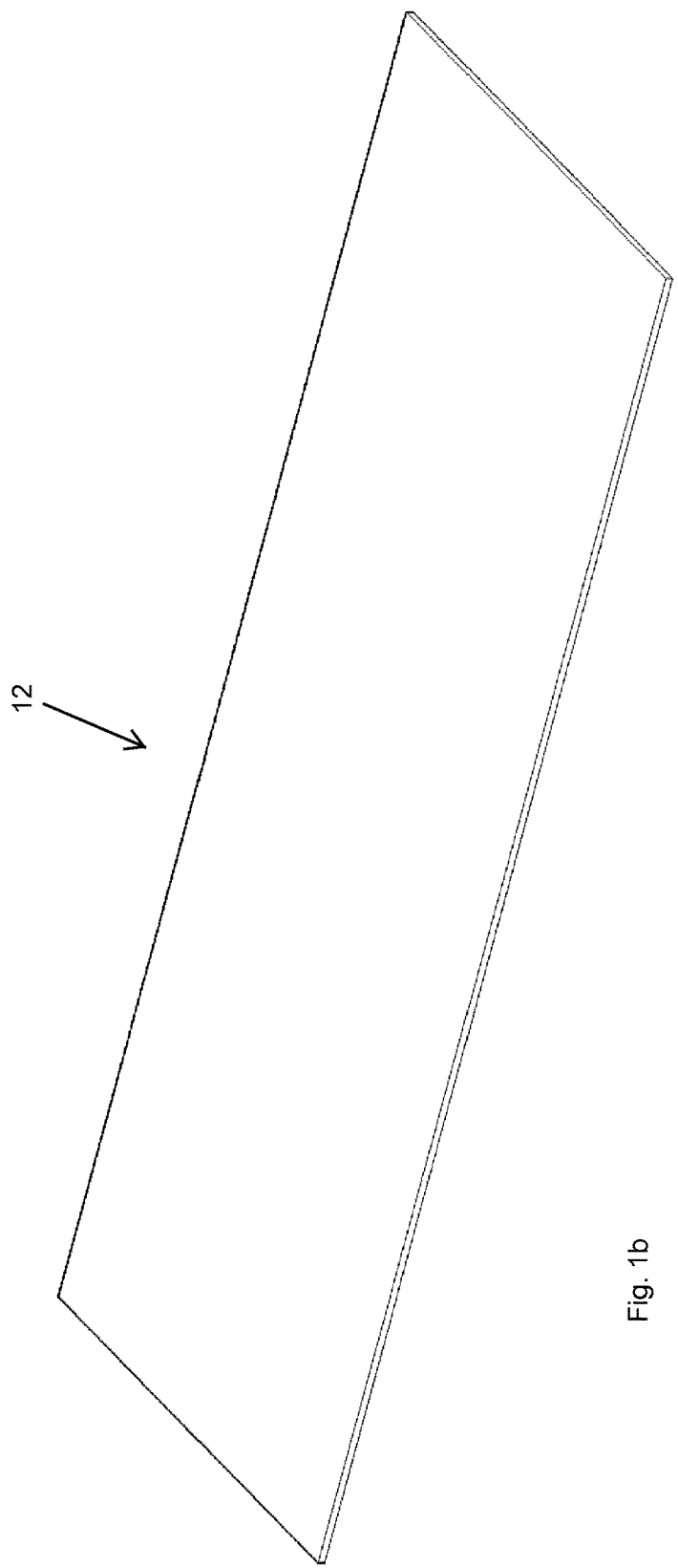
FIG. 1b illustrates a perspective view of the stretched sheet of material as illustrated in FIG. 1a, for use in manufacturing the device of the present invention.

The main constituent of the device 10 is a polymer, which may be bio-absorbable or non-absorbable, and may for example be one or a mixture of polymers such as PLA, UHMWPE, PEEK, PU, PTFE, PDO or other. This polymer or polymer mix is preferably initially cast into a blank or small sheet of material as illustrated in FIG. 1a. This sheet is then stretched as indicated in FIG. 1a, to produce a sheet or film 12 of increased surface area but reduced thickness.

The sheet or sheets 12 are preferably stretched, or alternatively cut to a specific size and/or shape that approximately equates to the volume of the final form of the device 10. By stretching the sheets, either uniaxially or biaxially, the polymer chains forming the sheet are both orientated to align with the axis along which the sheet is stretched, in addition to being compressed into closer proximity with one another such as to give a higher density of polymer chains. Thus while the stretched sheet will have a reduced thickness, it will have a higher density of polymer chains, which are also "oriented". Where the sheet is biaxially stretched the chains will tend to orient themselves radially. The sheet or sheets 12 of material will thus, as a result of the uniaxial or biaxial orientation, impart superior mechanical characteristics to the final device 10, when compared to a non oriented film or sheet of material. In addition, where multiple sheets 12 or layers are employed, the above mentioned uniaxial or biaxial orientation may be varied between layers to again increase the strength of the finished product.

Figure 2:
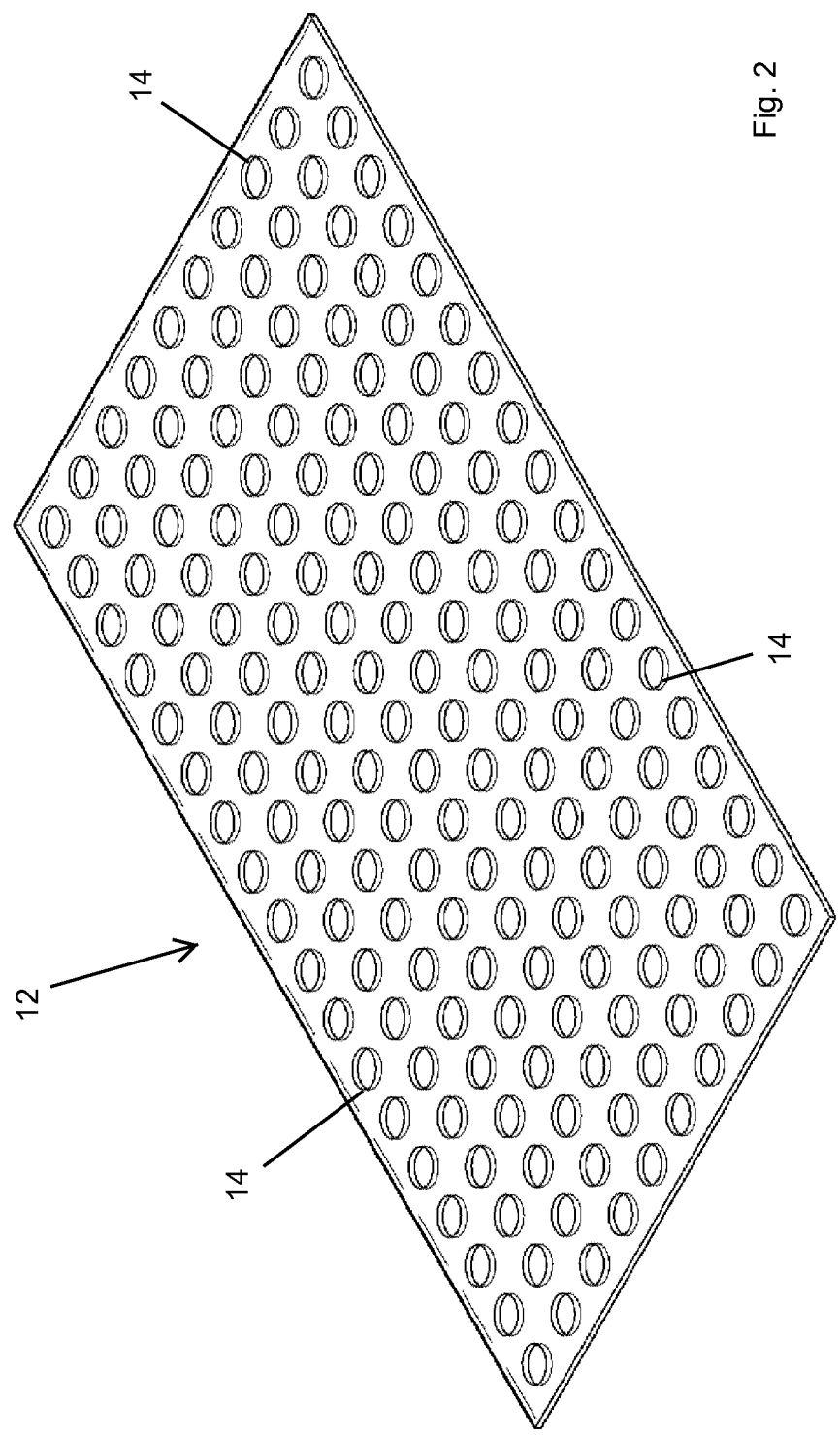
FIG. 2 illustrates the sheet of material of FIG. 1 having an array of pores formed therein.

Referring to FIG. 2, porosity is introduced into the sheet 12 by strategically removing material, although it is also envisaged that the sheet 12 could be initially produced with the porosity integrally formed therein, thus avoiding the additional step of removing said material in order to produce the porosity illustrated in FIG. 2. The method of introducing the porosity may for example be by means of laser cutting, rotary die, and perforation equipment of any other suitable alternative.

Individual pores 14 formed in the sheet 12 may vary in size and/or shape in order to achieve a desired functionality in the final formed device 10, as will be described in detail hereinafter. In addition the particular distribution of the pores 14 may also be varied as required. It will therefore be appreciated that the substantially rectangular array of pores 14 illustrated in FIG. 2 is merely an exemplary arrangement which is not intended to be in limiting.

Figure 3:
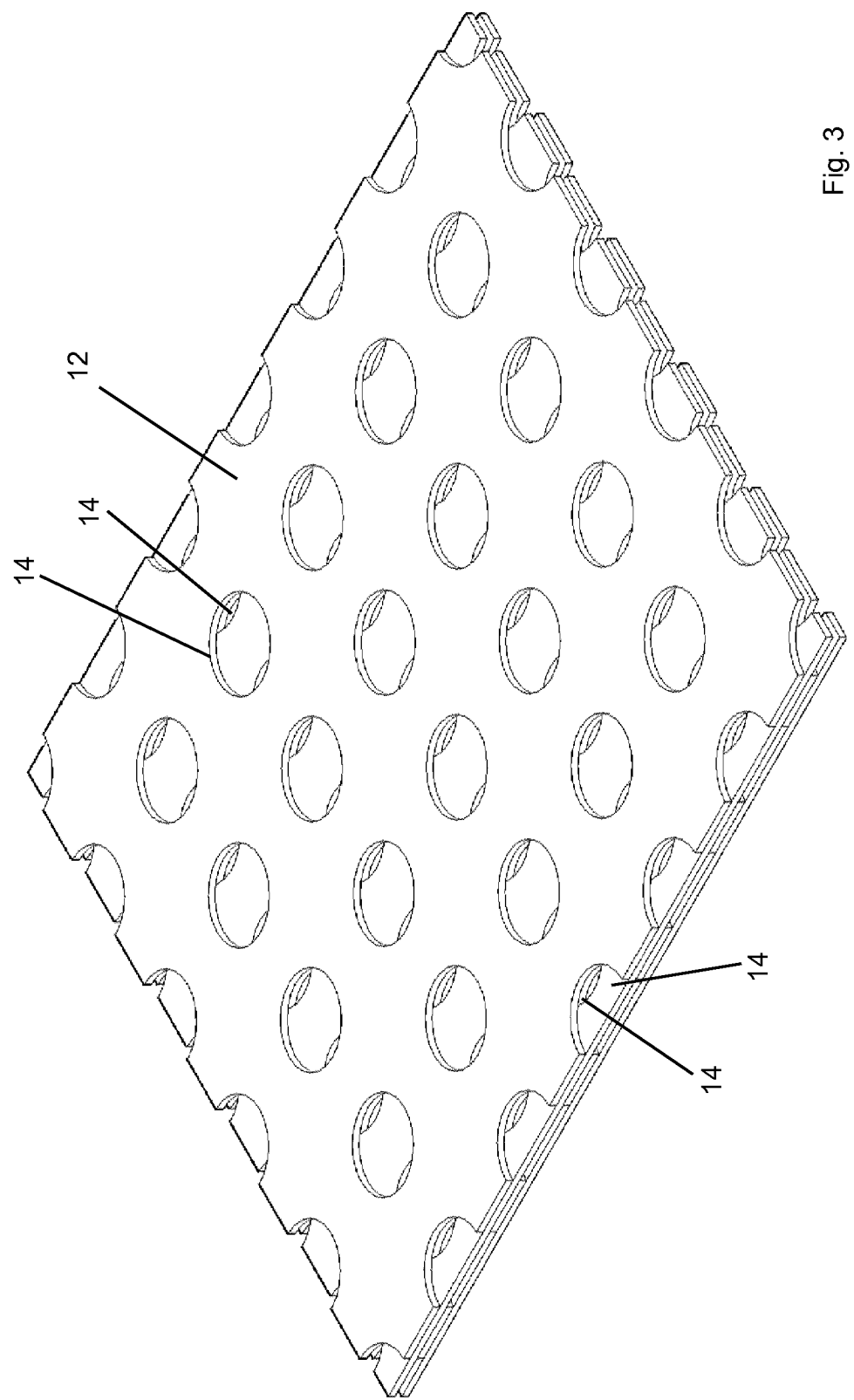
FIG. 3 illustrates multiple overlapping layers of the sheet material of FIGS. 1 and 2.

In producing the device 10 of the illustrated embodiment, in addition to any other form of device according to the present invention, it is a requirement that several layers of the sheet material 12 are stacked together such as to create areas or spaces of overlapping pores 14, as illustrated in FIG. 3. These spaces or passageways preferably extend from an exterior surface 18 of the finished device 10 to an interior surface 20, thus providing pathways for tissue ingrowth in order to establish a robust interface between the device 10 and the surrounding bone or other tissue, once the device 10 has been implanted. This process will be described in greater detail hereinafter.

While multiple layers of the sheet material 12 may be stacked in numerous different configurations and utilising numerous different methodologies, a preferred embodiment of the method of manufacture of the device 10 will now be described, in particular with reference to FIGS. 4-8.

Figure 4A:
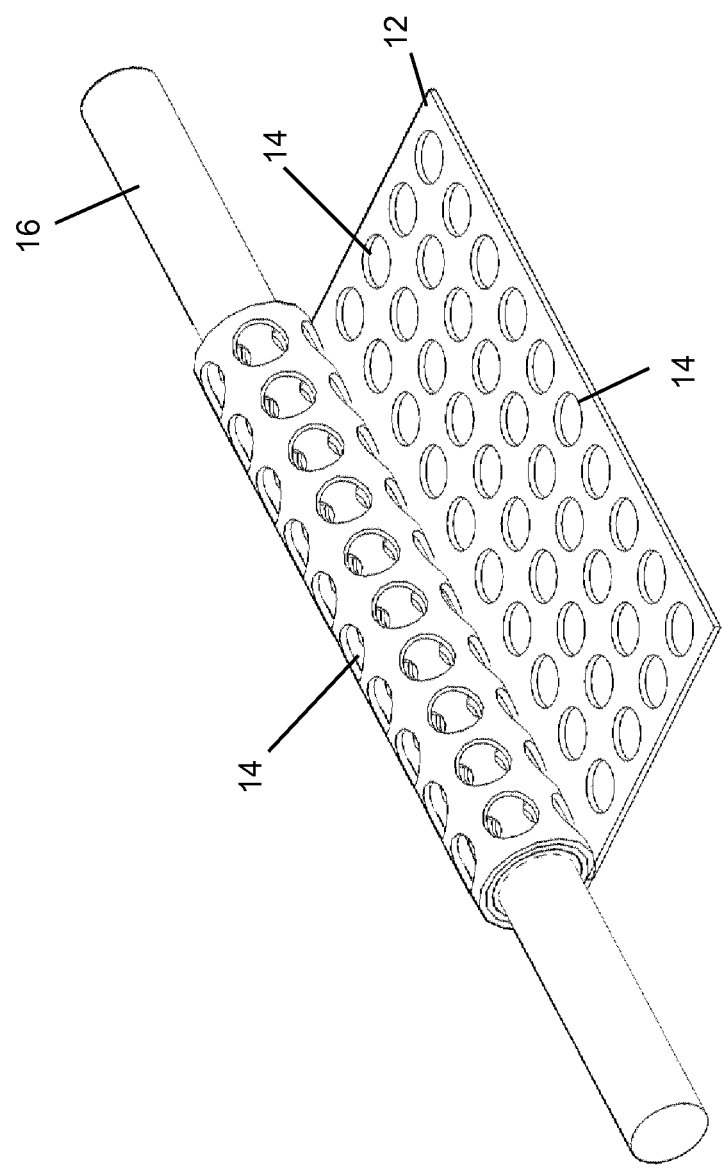
FIG. 4a illustrates a perspective view of the sheet material partially wound onto a mandrel.

Referring to FIG. 4a a mandrel 16 is illustrated onto which a single sheet 12, in which the array of pores 14 is provided, is partially wound onto the mandrel 16. Multiple sheets 12 could of course be wound onto the mandrel 16, although it is preferred to simply size the sheet 12 such that only a single sheet 12 is required to provide the necessary shape and volume. In this way it will be appreciated that multiple essentially concentric layers of the sheet material 12 are formed around the mandrel 16, in which adjacent layers have overlapping pores 14 in order to create the abovementioned spaces or pathways through the finalised form of the device 10. It is to be understood that while this methodology is particularly suited to the production of substantially cylindrical end products in which the overlapping layers are generated by winding one or more sheets around a mandrel, any other shape of end product could be produced once the necessary overlapping layers are present, regardless of the method employed to achieve the overlapping structure.

FIG. 4B illustrates the mandrel 16 when the sheet 12 has been fully wrapped in order to define a tubular construct of concentric layers of the sheet material 12. It is preferable, again for reasons set out in detail hereinafter, that the pores 14 are distributed in such a way that there are defined at least a number of pathways between overlapping pores 14 which extend from the exterior surface 18 of the device through to the interior surface 20 (shown in FIG. 9) of the device.

Referring now to FIG. 5 the fully wound mandrel 16 is placed into a suitable compression tool 22 having first and second halves 24, 26 between which is defined a cavity 28 shaped and dimensioned to receive the fully wound mandrel 16. Thus the halves 24, 26 are suitably separated and the fully wound mandrel 16 located therebetween and aligned or seated into one side of the cavity 28. The halves 24, 26 are then closed with pressure and heat then being applied for a specified time in order to at least partially laminate the wrapped layers of the sheet material 12. This step in the manufacturing process produces a partially cross laminated porous structure. It will be appreciated that any other functional alternative to the compression tool 22 may be employed in order to achieve the above described lamination of the layers of the sheet 12. The temperature profile during this lamination step may be controlled in order to alter the physical properties of the laminated product, and in particular may be utilised to alter the crystalline/amorphous nature of the final construct. The temperature profile employed should be such as to achieve the desired alteration of the physical properties of the sheet material 12 in order to facilitate lamination of the overlapping layers, while avoiding any significant reduction or reversal of the orientation achieved through stretching the sheet material 12 prior to layering.

Referring to FIG. 6 the partially laminated sheet 12 is removed from the tool 22. The open pores 14 of this structure are then filled with a growth-promoting medium 30, for example tricalciumphosphate (TCP) or an alternative, which growth-promoting medium preferably then fills all of the spaces or pathways defined by the overlapping pores 14. The growth-promoting medium 30 is illustrated filling the pores 14 of the partially laminated structure. TCP or similar growth-promoting medium can be introduced to the pore network through processes such as pressure assisted injection, coating, dispersion or other.

As an alternative to introducing the growth-promoting medium 30 after the partial lamination in the compression tool 22, the growth-promoting medium 30 may be introduced into the sheet material 12 once the pores 14 have been formed therein, but prior to layering and compressing the sheet material in order to produce the partially laminated structure.

Referring now to FIGS. 7 and 8, this partially laminated and growth-promoting medium filled structure is then placed into a mould 32 which again may be of any suitable form, and in the embodiment illustrated comprises an upper half 34 and a lower half 36 between which is defined a recess 38. In the embodiment illustrated the recess 38 is a basic cylinder which will produce a final product that has a smooth cylindrical outer profile. The recess 38 may however be provided with a profiled sidewall or parts thereof which, in combination with the heat and pressure to be applied by the mould 32, will impart a corresponding profile to the outer surface 18 of the final form of the device 10. The profile to the applied to the outer surface 18 may be of any preferred form, for example barb like shoulders where the device 10 is to function as a suture anchor or the like, screw threads where the device 10 is to function as a surgical screw, or any other desirable features.

The partially laminated and growth promoting medium filled structure is located between the halves 34, 36 of the mould 32, which are then closed in order to capture the structure within the recess 38. Once the upper and lower halves 34, 36 are clamped together heat and pressure is applied to the partially laminated and TCP filled structure. This application of pressure and heat over a specified time period will impart the fully laminate the layers of the sheet 12 and will optionally impart any desired outer profile shape to the finished device 10. Again the temperature profile during this lamination step may be controlled in order to alter the physical properties of the fully laminated product In this particular embodiment no surface formations are generated in the outer face 18 of the device 10. However, referring to FIG. 10 an alternative final form of a tissue-integration device according to the present invention is shown, generally indicated as 110. In this alternative device 110 like components have been accorded like reference numerals, and unless otherwise stated perform a like function. The device 110 is manufactured in the manner described above, with the only difference being in the final moulding stage the recess 38 of the mould 32 is modified to incorporate a screw thread profile in the sidewall such that the final moulded device 110 incorporates corresponding surface formations in an outer face 118 which are in the form of helical threads. In this way the final device 110 is adapted for use as a surgical screw.

Figure 10:
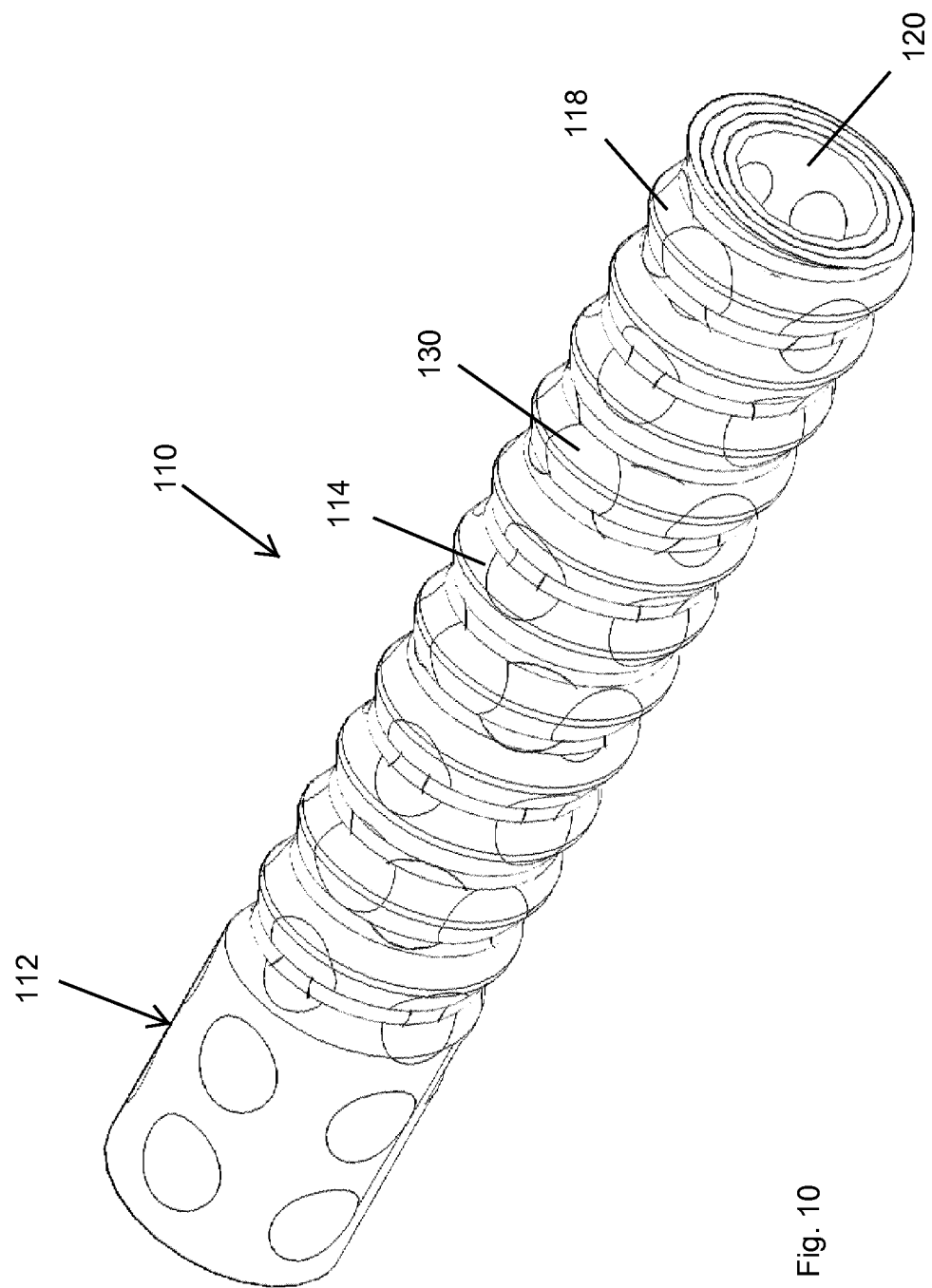
FIG. 10 illustrates a perspective view of an alternative final form of the device which can be manufactured according to the present invention.

Finally the device 10; 110 is removed from the mould 32 and the mandrel 16, with the finished form of the device 10; 110 illustrated respectively in FIG. 9 and FIG. 10. It can be seen that the device 10; 110 incorporates the filled pores 14; 114 which are accessible at the outer face 18; 118, and preferably the overlapping pores 14; 114 form multiple passages or paths extending from the outer face 18 through the device 10; 110 to the inner face 20; 120, thereby allowing, in use, tissue ingrowth to occur completely through the body of the device 10; 110, which results in a highly inductive structure for tissue ingrowth.

It will therefore be appreciated that the device 10; 110 of the present invention, in addition to the method of manufacturing same, provides both superior mechanical properties when compared to conventional injection moulded parts, in addition to allowing, through the precision location of the pores 14; 114, precise distribution of the growth-promoting medium throughout the structure of the device 10; 110. The superior mechanical properties arise from a combination of wrapping pre-orientated layers into a structure with effective cross-laminating of the individual-over-lapped-layers and in which polymer chains then impart a significant strength increase. In addition, controlling the degree/rate of temperature profiling during the lamination steps impacts the resulting crystalline/amorphous nature of the final construct The pathways through the device 10; 110 defined by the overlapping pores 14; 114 provide growth-promoting pathways filled with growth-promoting medium 30; 130 in order to encourage tissue ingrowth through the entire structure of the device 10; 110, resulting in an effective integration of the device 10; 110 into the tissue in order to ensure significant adhesion of the device 10; 110 to the surrounding tissue.

The invention claimed is:

1. A method of manufacturing a tissue-integration device, the method comprising the step of: overlapping layers of a porous sheet material to form the device and such as to create spaces defined by overlapping pores of adjacent layers; compressing the layers together to at least partially laminate the layers of the device, wherein the compression step is undertaken in two stages, wherein the first stage in the compression step comprises applying pressure to the layers before the addition of the growth-promoting medium to at least partially laminate the layers, wherein the second stage in the compression step comprises applying pressure to the partially laminated layers following the addition of the growth-promoting medium; and forming an outer profile on the device during the second stage of the compression step.

2. A method according to claim 1 comprising the step of at least partially filling at least some of the pores with a growth-promoting medium before or after the overlapping step.

3. A method according to claim 1 comprising the step of rolling the sheet material into a tube of concentric layers.

4. A method according to claim 1 comprising the step of wrapping the sheet material around a mandrel to establish the layers of the device.

5. A method according to claim 1 comprising the step of forming an outer profile on the device during the compression step.

6. A method according to claim 1 comprising overlapping the pores of adjacent layers such as to create at least one pathway between an outer and an inner surface of the device.

7. A method according to claim 1 comprising the step of applying heat to the sheet material during the compression step.

8. A method according to claim 1 comprising the step of orienting at least one of the layers of sheet material prior to overlapping.

9. A method according to claim 8 in which multiple layers of sheet material are oriented prior to overlapping and in which the orientation is varied between overlapping layers.

* * * * *